United States Patent [19]

Dardel

[11] Patent Number: 5,490,522
[45] Date of Patent: Feb. 13, 1996

[54] DEVICE FOR LOCATING AND PUNCTURING BLOOD VESSELS

[76] Inventor: Eric Dardel, Forrenbergstrasse 22b, CH-8472 Seuzach, Switzerland

[21] Appl. No.: 307,563

[22] PCT Filed: Jan. 14, 1994

[86] PCT No.: PCT/CH94/00007

§ 371 Date: Sep. 19, 1994

§ 102(e) Date: Sep. 19, 1994

[87] PCT Pub. No.: WO94/15532

PCT Pub. Date: Jun. 21, 1994

[30] Foreign Application Priority Data

Jan. 18, 1993 [CH] Switzerland ............................ 00127/93
Jul. 12, 1993 [CH] Switzerland ............................ 02084/93

[51] Int. Cl.⁶ .................................................... A61B 8/12
[52] U.S. Cl. ...................................................... 128/662.05
[58] Field of Search ........................ 128/661.08, 661.09, 128/662.03, 662.04, 662.05, 662.06

[56] References Cited

U.S. PATENT DOCUMENTS

| | | | |
|---|---|---|---|
| 3,556,079 | 1/1971 | Omizo | 128/2 |
| 3,721,227 | 3/1973 | Larson et al. | 128/662.05 |
| 5,131,394 | 7/1992 | Gehlbach | 128/662.05 |
| 5,131,395 | 7/1992 | Gehlbach | 128/662.05 |
| 5,235,987 | 8/1993 | Wolfe | 128/662.05 |

FOREIGN PATENT DOCUMENTS

| | | |
|---|---|---|
| 260953 | 3/1988 | European Pat. Off. . |
| 477581 | 4/1992 | European Pat. Off. . |
| 501410 | 2/1971 | Switzerland . |

OTHER PUBLICATIONS

Denys, B. G., et al, *An Ultrasound Method For Safe And Rapid Central Venous Access*, New England Journal of Medicine, No. 324, p. 566, Feb., 1991.

*Primary Examiner*—George Manuel
*Attorney, Agent, or Firm*—Walter C. Farley

[57] ABSTRACT

A non-sterile ultrasonic-Doppler unit (400/500/600) for locating and puncturing blood vessels is at least partly packed sterile with a sterile device (100/200/300), such that it can be used in a sterile field. The probe (600) of the ultrasonic-Doppler unit, has a slot (610) orientated in the axis of the ultrasonic field and is inserted into a sterile cap (300), causing a guide tube (340) for the puncturing needle penetrating this cap to lie in the slot of the probe. The device envelopes the probe completely, such that the non-sterile ultrasonic probe (600) does not contaminate the puncturing needle, the patient's skin nor the surgeon. The cap (300) can contain a coupling member, which guarantees ultrasonic coupling between the probe (600) and the patient's skin, such that the surgeon need not add any gel. All parts of the device are disposable single-use articles.

22 Claims, 12 Drawing Sheets

DEVICE FOR LOCATING AND PUNCTURING BLOOD VESSELS

FIELD OF THE INVENTION

The invention relates to a device, which, in connection with an ultrasonic-Doppler instrument and a puncturing needle, permits non-invasive location and puncturing of blood vessels in a sterile area. The ultrasonic-Doppler instrument is non-sterile and intended for repeated use. Prior to use it is packed to be sterile with the aid of the inventive device.

BACKGROUND OF THE INVENTION

It is known that ultrasonic instruments can be useful in puncturing central veins and arteries. This more particularly applies in the case of image-forming ultrasonic instruments, on whose screens can not only be seen a sectional image of the investigated body region but also the puncturing needle, which can considerably facilitate puncturing. Such a method is e.g. described in the New England Journal of Medicine, 324:566, February 1991. However, it is difficult to sterilize ultrasonic probes, so that prior to use they are packed in a sterile, tubular cover, as is e.g. described in EP-A1-477,581. Laterally it is possible to fix to the ultrasonic probe and over the sterile cover a sterile coupling piece, which guides the puncturing needle in the ultrasonic sectional plane, such that said needle is visible on the screen (as described e.g. in U.S. Pat. No. 4,898,178). However, such image-forming instruments are not sterilizable and are so large that it is scarcely possible to bring about the sterile packing thereof and consequently they need a large setting-down surface outside the sterile operating field. An at least two meter long electric cable then connects the ultrasonic probe to the electronic casing, which is disadvantageous in the confined space conditions of intensive care units or catheterization units.

It is also known to use for the same purpose Ultrasonic-Doppler, which only reproduce acoustic signals and can therefore be much smaller and cheaper than the image-forming instruments. In most cases of such Doppler units the puncturing needle is virtually identical with the ultrasonic field axis. Therefore the piezocrystals of the ultrasonic probe and the puncturing needle are so spatially close together, that the ultrasonic probe is contaminated by the patient's blood. This, in particular applies to instruments, in which the piezocrystals are located within the needle or syringe, as described in U.S. Pat. Nos. 3,556,079, 5,131,394 and EP-A-260,953. The same contamination takes place if the ultrasonic probe is placed around the needle, as e.g., in CH-A-501,410. The contaminated ultrasonic probes can be gas-sterilized, but this process is time-consuming and also significantly reduces the life of the expensive ultrasonic probes. It is also expensive to dispose of the ultrasonic probe after a single use, as is recommended by certain manufacturers.

In EP-A1-0'516'582 a device is described, with which a non-sterile ultrasonic probe can be used, as it cannot contaminate neither the puncturing needle, nor the surgeon's gloves, nor the patient. A sterile coupling element, is planted on the non-sterile ultrasonic probe. In this coupling element the ultrasonic field is diverted by means of a mirror, such that the puncturing needle, guided by the coupling element, is directed towards the patient's skin parallel to and in the center of the ultrasonic field. The distance between the puncturing needle and the ultrasonic probe corresponds to at least half the diameter of the ultrasonic probe, such that the puncturing needle is unable to be contaminated. The coupling element must be manufactured to a high level of precision, because the ultrasonic probe, the mirror and the needle must be precisely positioned in relation to one another. Additionally the coupling element must be filled without gap with ultrasonic conducting gel and sealed with a puncturable elastomer membrane to prevent the gel from flowing out. Thus the coupling element, which is intended for single use, is relatively expensive.

Most known devices for sterile packing of ultrasonic units imply the collaboration of a sterile and a non-sterile person, as described in EP-A1-0'477'581 and EP-A1-0'516'582. According to EP-A1-0'540'461 a non-sterile person can hand the probe to a sterile person in the usual way. In this case however the two electric cables and the two electronic plugs that connect the ultrasonic probe with the electronics are part of the single use part of the whole instrument, which therefore makes this single-use part expensive.

SUMMARY OF THE INVENTION

An object of the invention is to provide a device for non-invasive location and puncturing of blood vessels in a sterile area. This device is intended to be used together with an ultrasonic-Doppler unit with the associated probe and with a puncturing needle, whereby the ultrasonic-Doppler unit and especially the probe need not be sterile. The device is intended for single use and therefore is not to be expensive. It must be possible for a non-sterile person to assemble the device with the non-sterile parts in a usual way, together with a sterile person or alone immediately before use. By means of the device it must be possible to direct the puncturing needle parallel to and in the center of the ultrasonic field towards the patient's skin and also to bring the probe near enough to the patient's skin, so that location of a vessel is possible even without a coupling member. The handling of the device must be at least as simple as the handling of known devices for the same purpose.

The puncturing instrument as described by the invention essentially comprises on the one hand a non-sterile ultrasonic-Doppler unit, which can emit acoustic and/or optical signals and on the other hand a device according to the invention, which is essentially a sterile package, comprising a cap for contact with the patient's skin and a preferably flexible packaging element that is attached to the cap. The flexible packaging element consists e.g. of a piece of flexible tube that is sealed with the cap on one end and is sealable on the other end. Immediately before use of the puncturing instrument the non-sterile Doppler unit is inserted into this sterile packing, which is then closed, such that the outside of the packing stays sterile and can be used in sterile areas such as an operating theatre. The cap is designed so that it holds the probe of the ultrasonic Doppler unit in a defined position relative to a guide tube integrated in the cap, such that the axis of the guide tube essentially corresponds to the axis of the ultrasonic field. The sterile package is closed when in use and the guide tube for the puncturing needle, going right through the cap, prevents contamination by the non-sterile ultrasonic probe of the puncturing needle, the patient, and the surgeon's gloves. After use, the inexpensive sterile device (cap and flexible tube) is discarded. Neither the ultrasonic unit, nor the probe to be sterilized prior to the next use.

The ultrasonic-Doppler unit can be battery-operated and have pocket size, so that no special setting-down surface is required. As a result the electric cable connecting the ultrasonic probe to the remainder of the electronics can be correspondingly short, which permits easy insertion of the non-sterile unit into the sterile device.

The ultrasonic Doppler unit may, however, be larger whereby the electronics casing and the probe are connected with a longer cable, such that the electronics casing can be placed outside the sterile field and consequently need not be sterile packed. In order for such an instrument to locate the optical directional indication in the viewing field of the surgeon all the same, it is advantageous to place the directional indication on the probe casing and not on the electronics casing. In this embodiment the cable can be sterilized, so that only the probe needs sterile packing.

The cap may contain a coupling member, which facilitates the mechanical coupling between the ultrasonic probe and the patient's skin. This coupling member is preferably made from a dimensionally stable, aqueous gel, because such gels have a low ultrasonic absorption. However, such gels are slippery and must therefore be fixed to the cap with special retaining means. The coupling member can be fixed by means of a special structure of the cap's wall (porous material with through-bores). In a variant the coupling member is fixed by means of a net or a membrane that runs diagonally through the gel and is fixed to the wall of the cap. However, the coupling member can also be made from a rigid plastic, which is not slippery, so that no special retaining problems occur.

The device according to the invention is intended as a disposable article and is preferably made from plastic, whereby individual components such as the needle guide can also be metallic or ceramic. The coupling member can be made from ultrasonic-conducting plastic or aqueous gel.

BRIEF DESCRIPTION OF THE DRAWINGS

The invention is described in greater detail hereinafter relative to non-limitative embodiments and the attached drawings, wherein.

Figure 1:
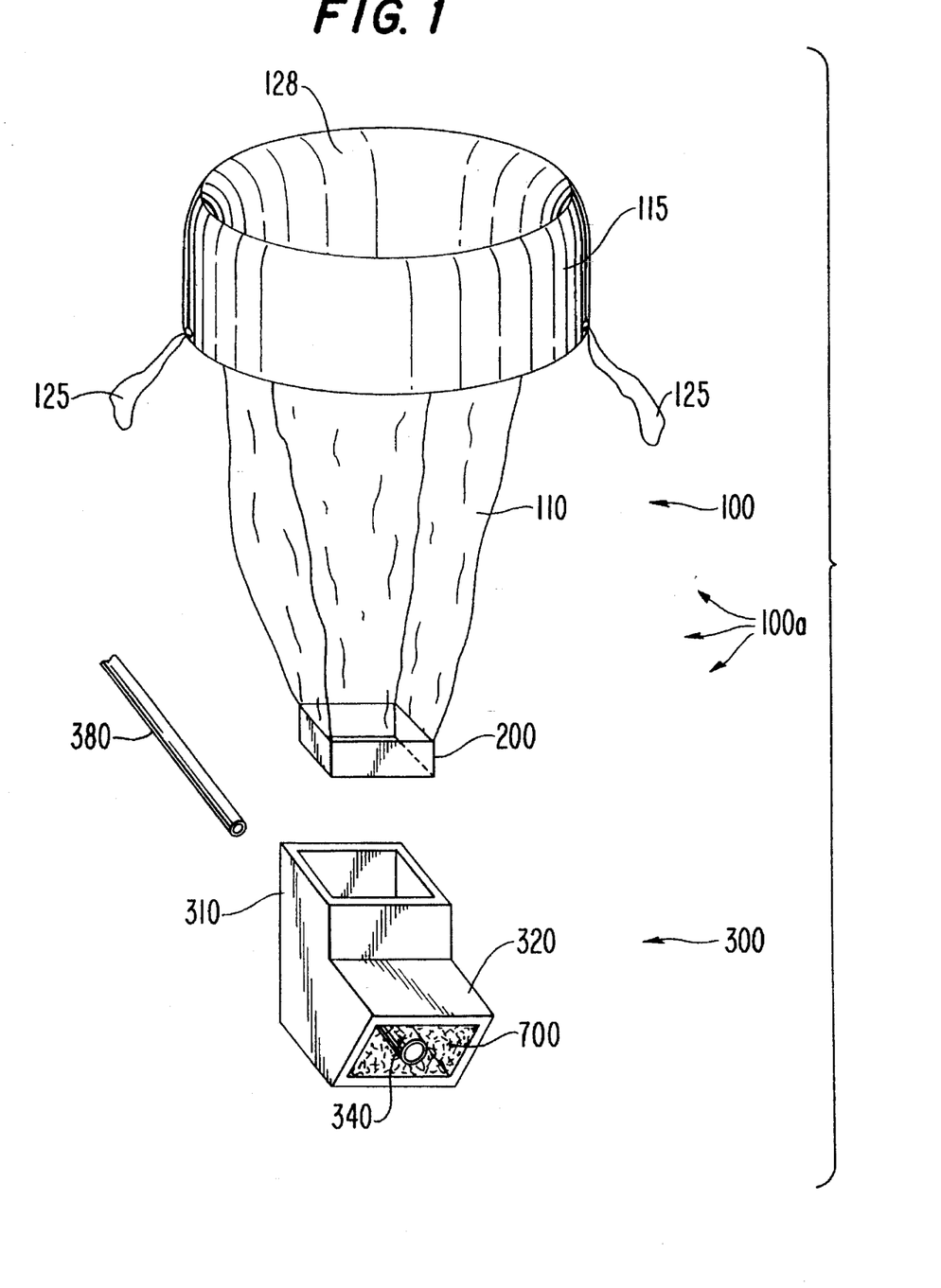
FIG. 1 is a perspective, exploded view of the sterile disposable parts of a device according to the invention.

FIG. 1 shows an exemplified embodiment (100a) of the device according to the invention. It consists essentially of a flexible tube 100 (flexible packaging element), a cap 300 and a frame 200 forming a connection between the cap and the flexible packaging element. Prior to inserting the ultrasonic-Doppler unit through the opening 128 of the tube 100, the upper end 115 thereof is inverted backwards, i.e., folded out and down. At the lower end of the tube 110 is fixed the frame 200, which permits a mechanical connection between the flexible tube 100 and the rigid cap 300. If the cap 300 is engaged on the frame 200, together with the tube 100 they form a cavity, which only has one opening 128, e.g. closable with ribbons 125. The cap 300 features a guide part 310 for the probe and a coupling member part 320 with a coupling member 700. A guide tube 340 for the puncturing needle 380 penetrates both parts 310 and 320 of the cap.

Figure 2:
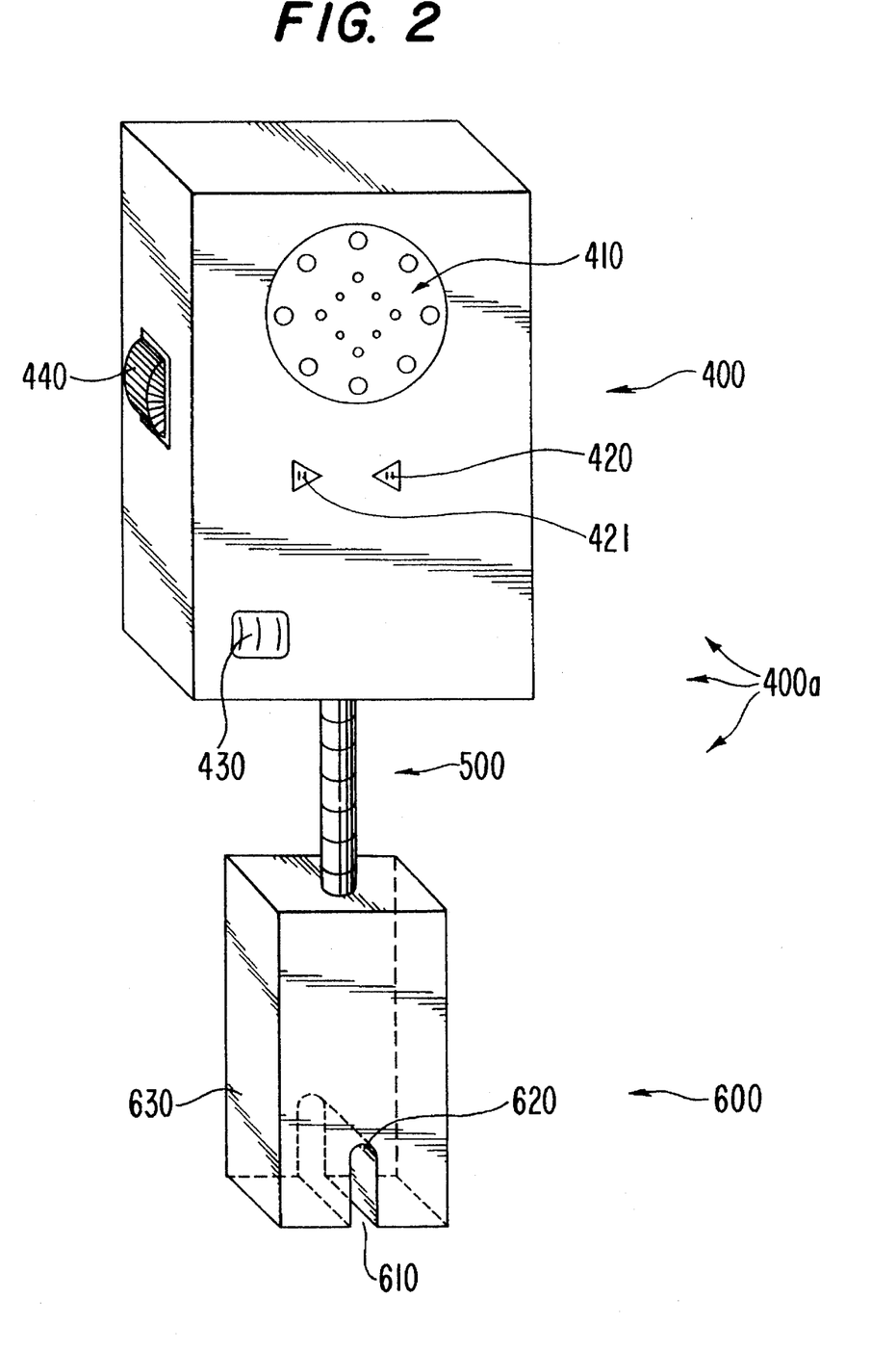
FIG. 2 is a perspective view of an ultrasonic Doppler unit, that can be packaged with the device according to FIG. 1.

FIG. 2 shows an example of an ultrasonic Doppler unit 400a, that can be packaged in a non-sterile condition with the device according to FIG. 1. It comprises an electronics casing 400, an electric cable 500 and an ultrasonic probe 600. On the casing 400 are provided an on/off switch 430, a loudspeaker 410, a control knob 440 for volume regulation, as well as a visual display 420, 421 for indicating the bloodstream direction. If the emitted ultrasonic waves and the flowing blood move substantially in the same direction then e.g. the visual display 420 lights up and if the two directions are substantially opposite to one another then the visual display 421 lights up. The combination of acoustic and optical signals is appropriate, because it can facilitate the differentiation between veins and arteries.

The ultrasonic probe features in a per se known manner a slot 610, that is oriented such that the axis of a guide tube for a puncturing needle inserted into the innermost part 620 of the slot is directed towards the center of the emitted ultrasonic field and parallel to it.

Figure 3A:
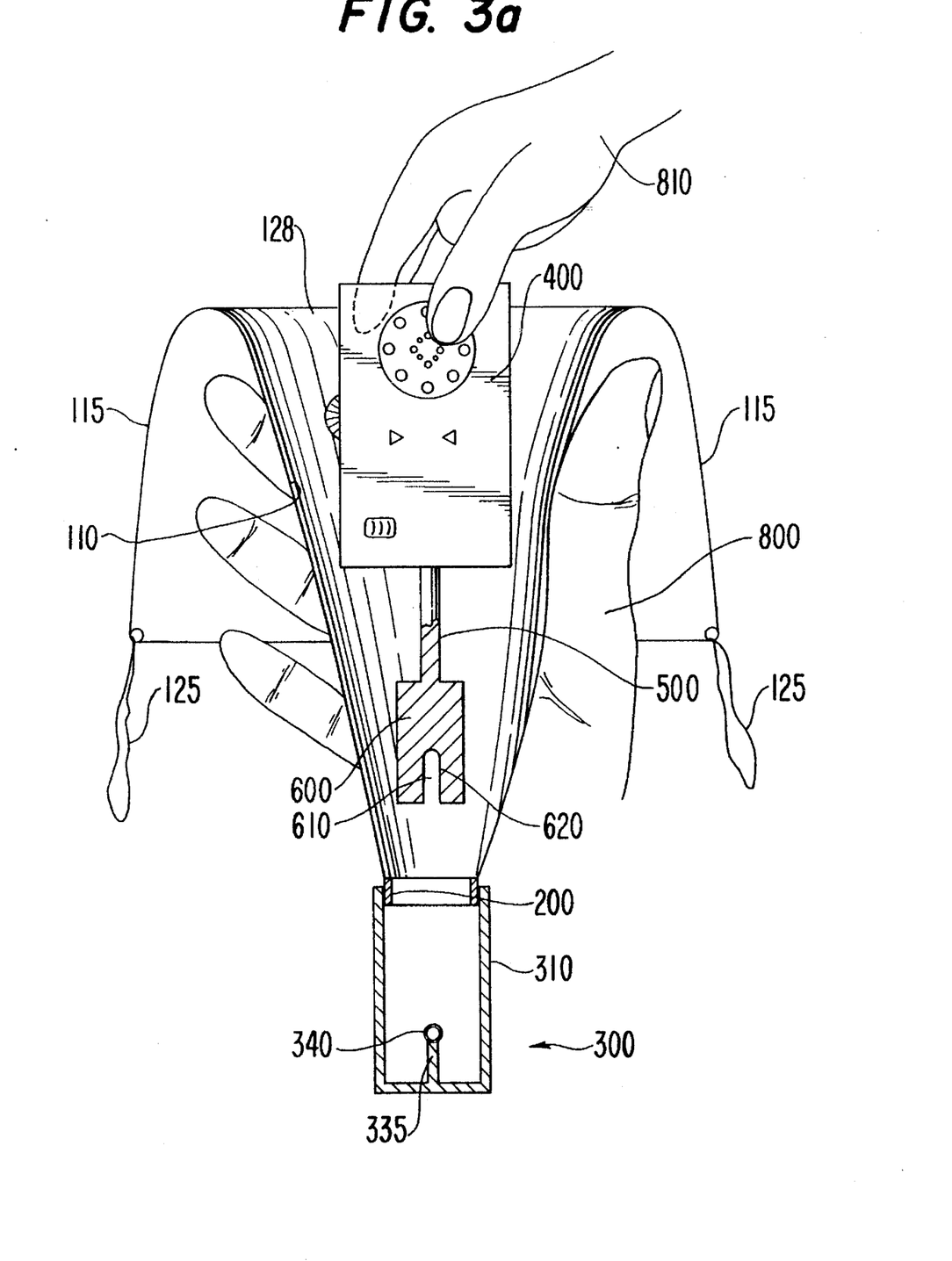
FIGS. 3a and 3b are side elevations, partly in section, showing two phases of the procedure for sterile packing the Doppler unit according to FIG. 2 by means of the device according to FIG. 1.
Figure 3B:
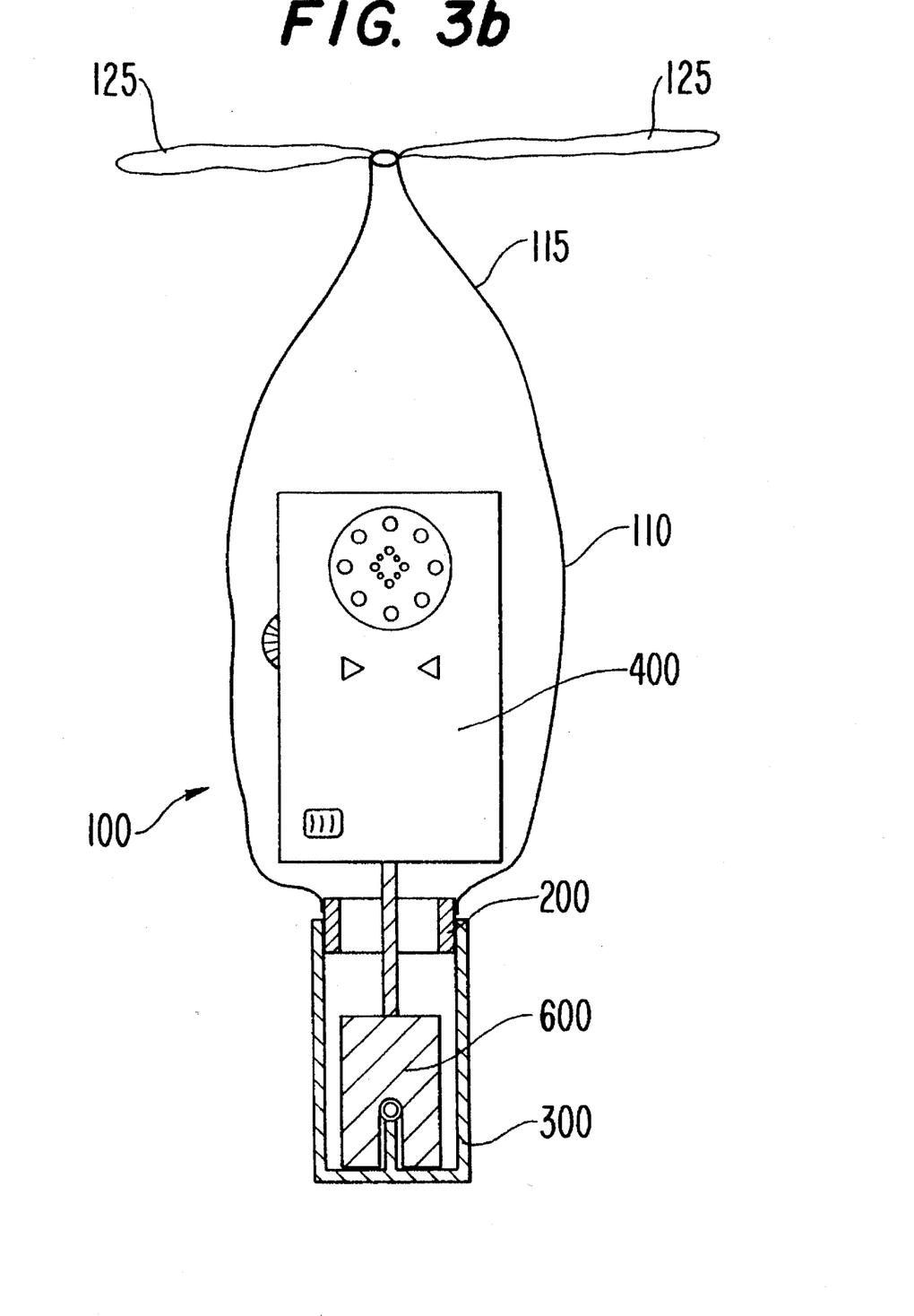

In FIGS. 3a and 3b two phases of the insertion of the non-sterile ultrasonic Doppler unit 400a (FIG. 2) into the inventive device 100a according FIG. 1 are shown. A sterile hand 800 is inserted between the inverted part 115 and the non-inverted part 110 of the packaging element 100 (FIG. 3a), so that said hand 800 is protected against contamination by the non-sterile unit 400a. The non-sterile person with the hand 810 guides the non-sterile unit 400a into the opening 128 of the packaging element 100. Using the not shown second hand, the sterile person raises the inverted part 115 of the packaging element 100 (FIG. 3b) and with the aid of the two ribbons 125 closes the top of the tube 100. Thus, the non-sterile unit 400a packed into the device 100a is usable in sterile areas. The flexible packaging element 100 can obviously also be closed by other means, such as minigrips, clamps or adhesives.

The ultrasonic probe 600 is then advanced by the sterile person through the flexible packaging element 100 into the cap 300. The probe 600 is guided by the guide piece 310 of the cap 300 and is advanced into the same until the guide tube 340 is stopped in the innermost part 620 of the slot 610.

Figure 4:
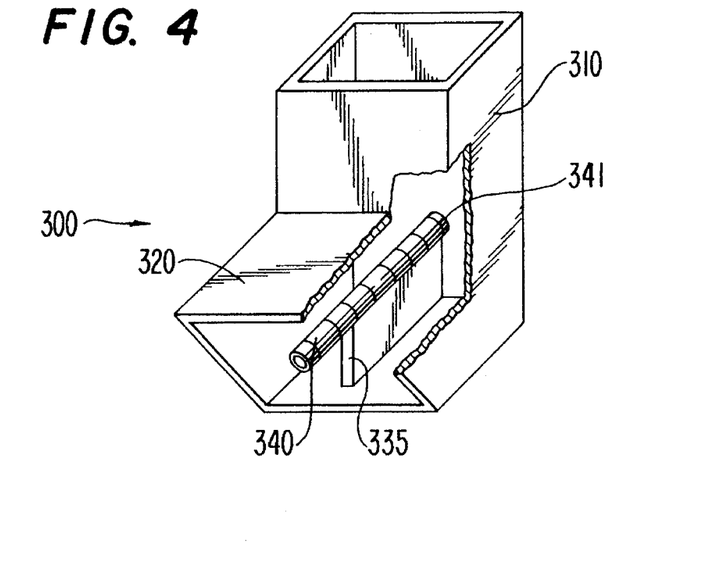
FIG. 4 is a perspective view of a cap for the device according to the invention.

The guide tube 340 can be fixed to a web 335 (see also FIG. 4). As the innermost part 620 of the slot 610 is orientated in the direction of the emitted field, a puncturing needle 380 (FIG. 1) inserted through the guide tube 340 also approximately coincides with the ultrasonic axis and can therefore puncture a located vessel.

Figure 9:
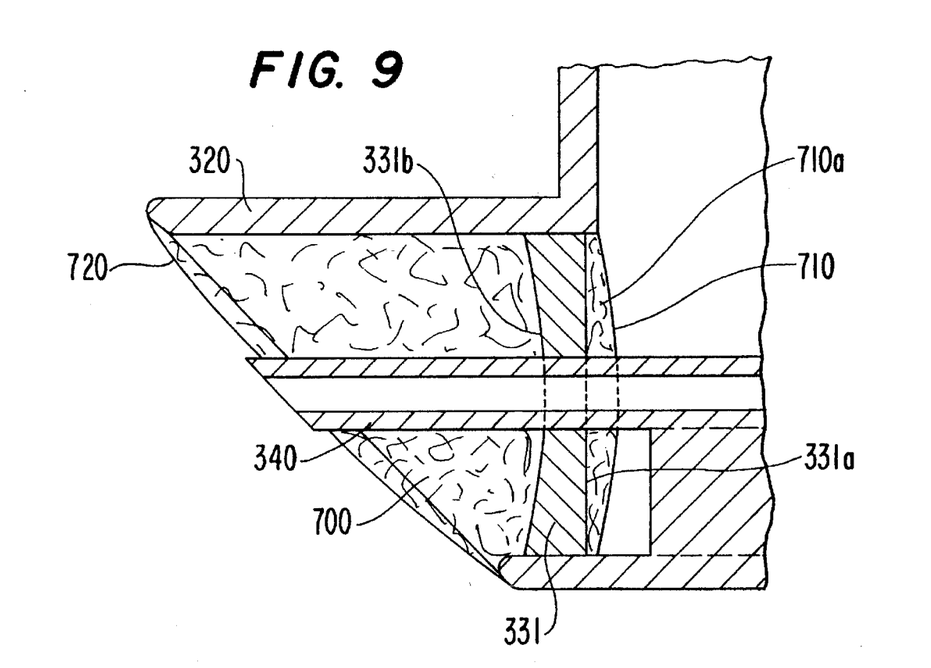
Figure 10:
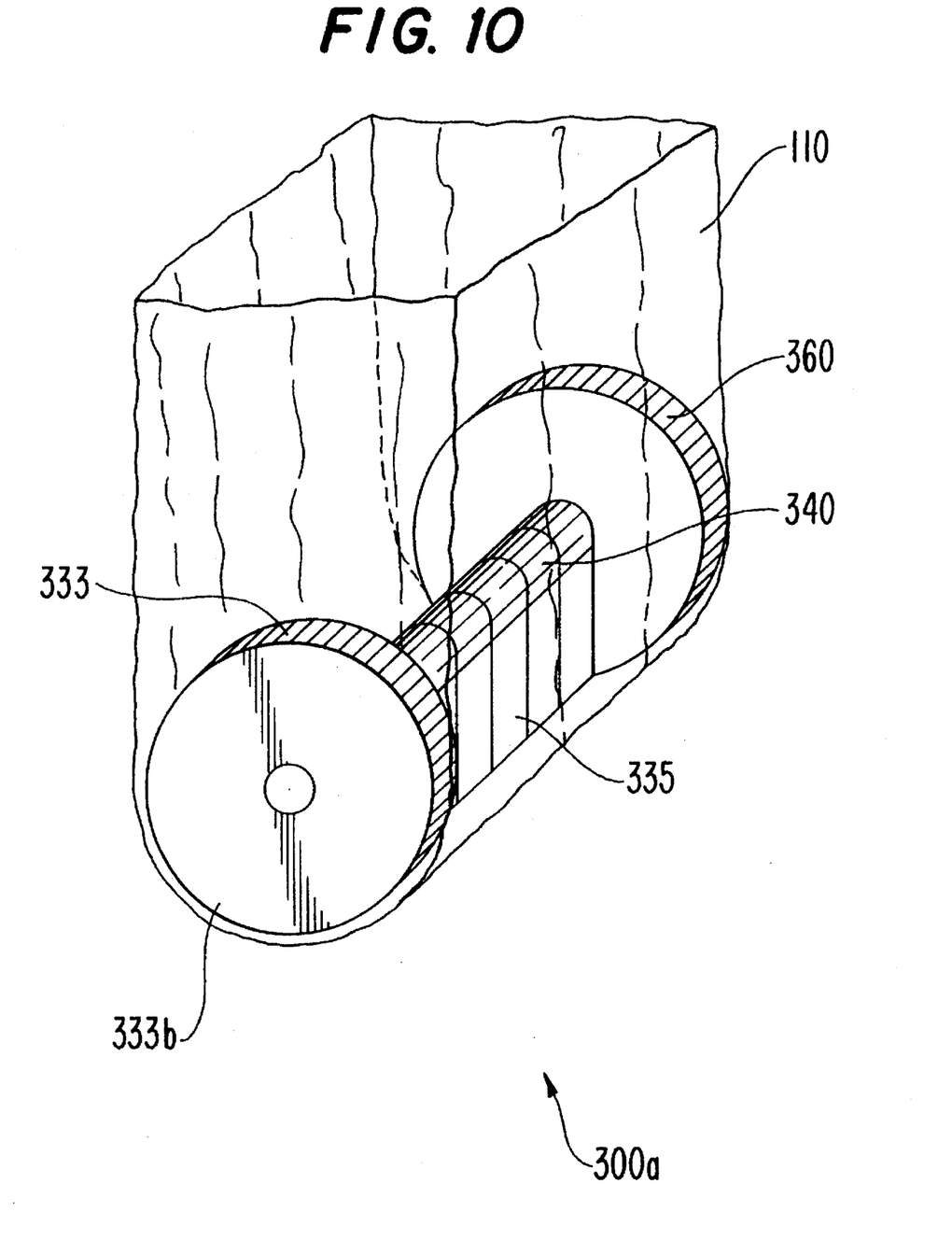
FIG. 10 is a perspective view of a further variant of the device according to the invention.

As the ultrasonic probe can be brought extremely near to the patient's skin with the help of the device according to the invention, the coupling member can be left away (see the description in connection with FIG. 10). If a coupling member is used all the same it will facilitate the coupling between the ultrasonic probe and the patient's skin. FIGS. 5 to 9 and 11 to 12 show, in section, embodiments of caps with coupling members.

Figure 5:
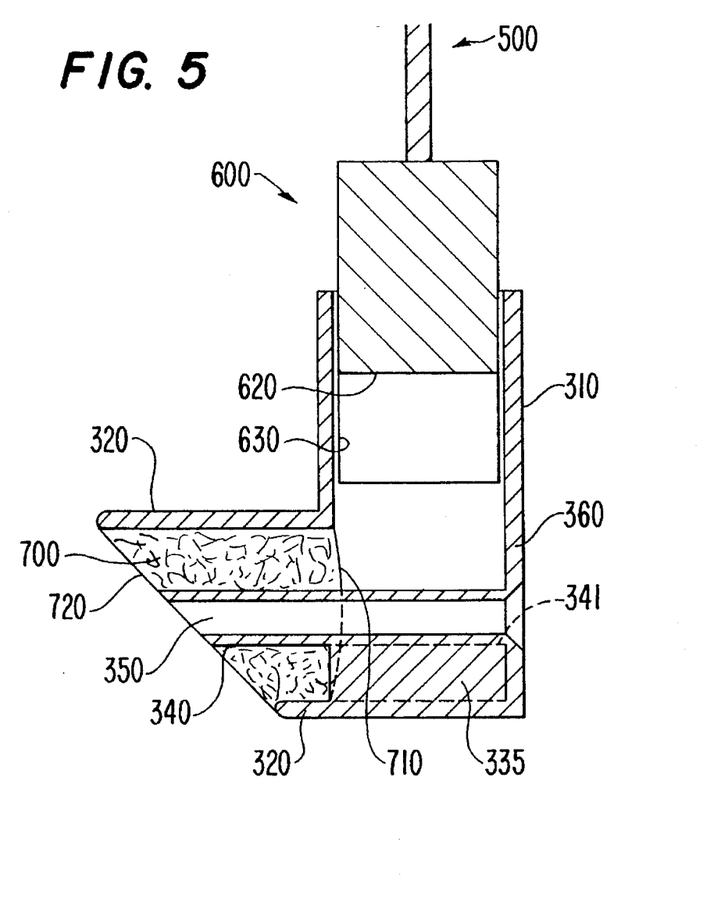
FIGS. 5 to 9 are side elevations, in section, through different variants of caps with coupling members.

The variant according to FIG. 5 has a coupling member 700 consisting e.g. of a dimensionally stable aqueous gel, that has a limited ultrasonic attenuation and due to its deformability permits good coupling to the ultrasonic probe. The probe-side surface 710 of the coupling member 700 is slightly convex and is somewhat displaced by the advance of the ultrasonic probe 600, so that no air remains between the end face 630 of the probe 600 and the coupling member surface 710.

Figure 6:
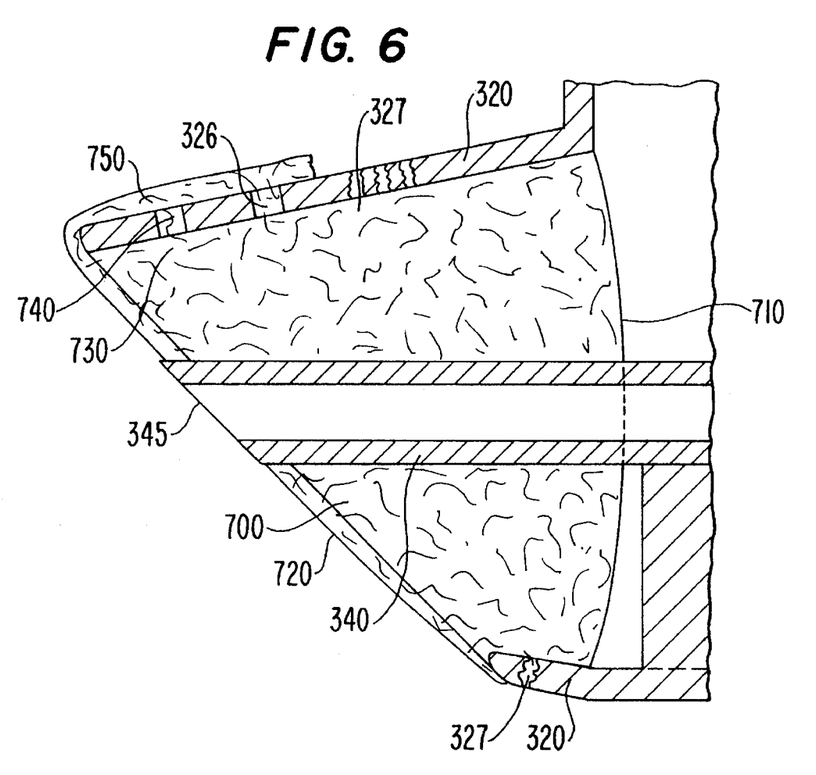
Figure 7:
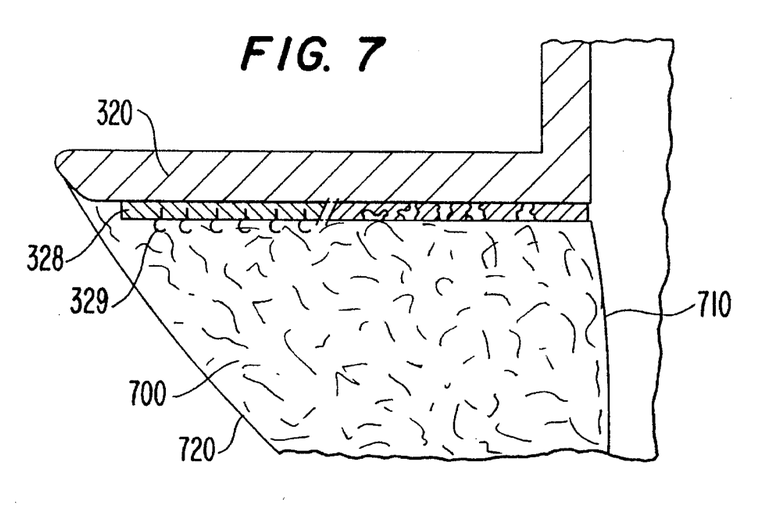
Figure 8:
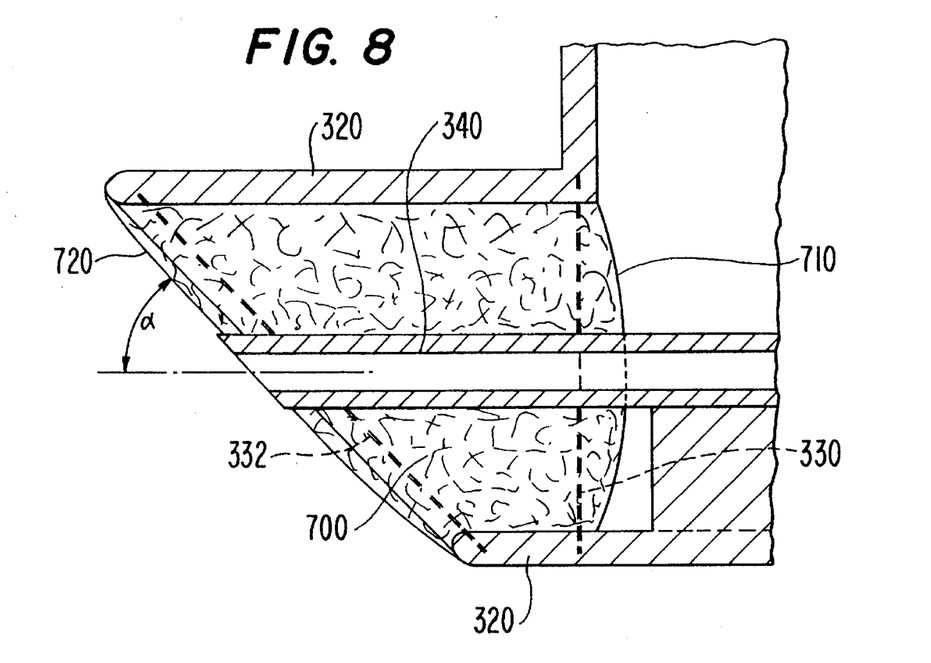

Dimensionally stable, aqueous gels are very slippery, so that the insertion of the ultrasonic probe 600 into the cap 300 could give rise to the coupling member 700 being pressed out of the coupling member part 320 of the cap. To prevent this the coupling member part 320 can be conical, as shown in FIG. 6, and/or it can consist of porous material such as e.g. sintered polyethylene. On molding the coupling member 700 the still liquid gel penetrates the pores 327 of the coupling member part 320, so that there is a firm anchoring in the solidified state. In place of the pores 327, it is also possible to have several holes 326 in the coupling member part 320, so that the coupling member 700 substantially surrounds part 320 and gel strands or connecting points 740 connect an inner piece 730 and an outer piece 750. In another variant (FIG. 7) the inner face of the coupling member part 320 is provided with a covering 328, such as e.g. a Velcro layer with small hooks 329 or a thin sponge on which the gel can be anchored.

In order that a puncturing needle 380, inserted through the guide tube does not punch out any material of the coupling member 700 and introduce the same in subcutaneous or intravascular manner, it is appropriate for the end 345 of the guide tube 340 to reach the body-side surface 720 of the coupling member 700, as shown in FIG. 6.

However, the coupling member 700 can also be held by a gauze 300 in the vicinity 330 of the ultrasonic probe 600 or on the body-side end (332) of the coupling member 700 (FIG. 8), which is transversely tensioned by the coupling member part 320 of the cap and fixed to the latter. The coupling member 700 which is still liquid at the time of molding penetrates through the meshes of the gauze 330 or 332 and is then firmly connected thereto in the solidified state.

In place of a thin gauze it is also possible to provide on the probe side a fixed plate 331 (FIG. 9), which can be a component of the cap 300. The plate 331 completely separates the ultrasonic probe 600 from the coupling member 700, so that the latter is not displaced by the probe 600. The plate 331 can be made from plastic, which in the case of a thickness of 0.5 to 2 mm only has a low ultrasonic absorption. In order to ensure a good coupling between the end face 630 of the ultrasonic probe 600 and the inner face 331a of the plate 331, at least one of the two faces 630 or 331a should be coated with gel or a salt solution prior to the insertion of the probe 600 into the cap 300. The coating of the inner face 331a of the plate 330 can take place during the manufacture of the cap 300, in that a thin coating 710a of a similar material to that of the coupling member 700 covers face 331a.

The plate 331 can be made from a plastic, e.g. plexiglass, which has a higher sound propagation velocity than that of the aqueous coupling member 700. If the face 331b is concave, then the plate 331 has a focusing action on the ultrasonics. The disposable cap 300 can then additionally fulfill the function of a replaceable ultrasonic lens, whose focal distance can be optimized to the depth of the vessels to be located. If the plate consists of a material with a lower sound propagation velocity than the material of the coupling member, face 331b on plate 331 must be convex.

A rigid plastic can also be used as material for the coupling member 700, such as e.g. urethane rubber. Although such plastics have a higher ultrasonic absorption than aqueous materials, they are not slippery, so that no special measure is necessary for fixing them. The coupling member can then be arranged, as shown in the Figures, in a coupling member part 320 of cap 300. Coupling member and according wall can also be placed onto the cap as separate parts. If the material of the coupling member is rigid, actually no wall is necessary.

In order to achieve good coupling between the skin of the patient and the body-side face 720 of the coupling member 700 without pressure being exerted, it is advantageous for the face 720 to be positionable parallel to the skin, i.e. to form an angle of approximately 30° to 45° with the axis of the guide tube 340 (angle $\alpha$ in FIG. 8), similar to the angle between the puncturing needle and the blood vessel axis. Obviously an angle of 90° is also possible, but then the face 720 must be relatively firmly pressed onto the skin, as is usual with conventional ultrasonic probes.

FIG. 10 shows a further embodiment of the device according to the invention without a coupling member 700. In this variant the cap (only probe guide part) is reduced to guide tube 340, which, together with a facultative web 335, connects two plates 333 and 360. When using this embodiment a thin layer of gel, as it is common with conventional ultrasonic probes, is applied between the patient's skin and the front face 333b of the front plate 333. In this embodiment the flexible packaging element 110 is closed. The reduced cap 300a is positioned inside the packaging element, which is e.g. welded or glued to the front plate 333 and the rear plate 360. The puncturing needle (FIG. 1) can easily penetrate the thin packaging element.

For a skin contact area with an angle of 30° to 45° to the guide tube, plate 333 can be produced in the form of a wedge. In this case plate 333 preferably consists of a plastic suitable as coupling member (e.g. urethane rubber) or of an essentially tube shaped wall piece (e.g. plastic) that is surrounds a gel as coupling member, similar to the coupling member part of the cap described above.

Figure 11:
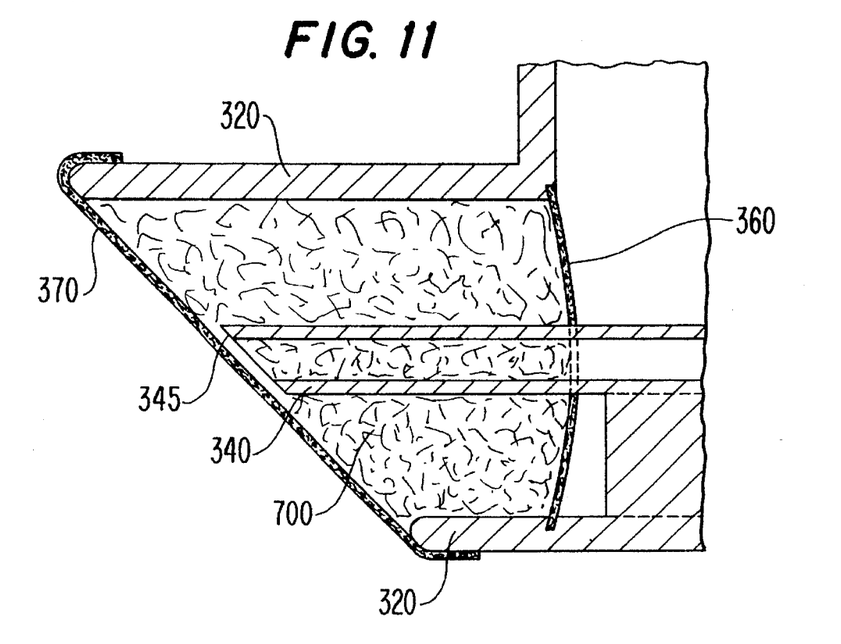
FIGS. 11 and 12 are sectional views through variants of caps with coupling members.
Figure 12:
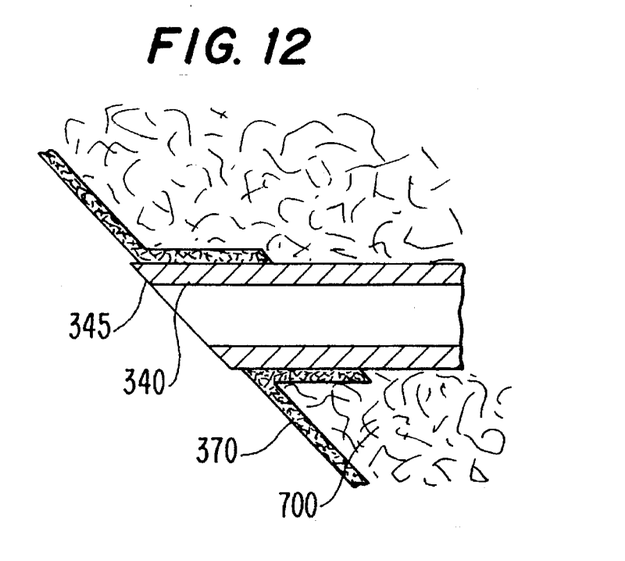

FIG. 11 shows a further embodiment of the cap with a coupling member 700 made from viscous gel. Both on the probe side and on the body side a flowing of gel out of part 320 is prevented by diaphragms or gauzes 360 and 370. The end 345 of the guide tube 340 can be located within the coupling member 700, in which case the diaphragm or gauze 370 must be perforated when puncturing. Perforation can be prevented by fixing the diaphragm or gauze 370 to the outer side of guide tube 340, as is shown in FIG. 12.

Figure 13:
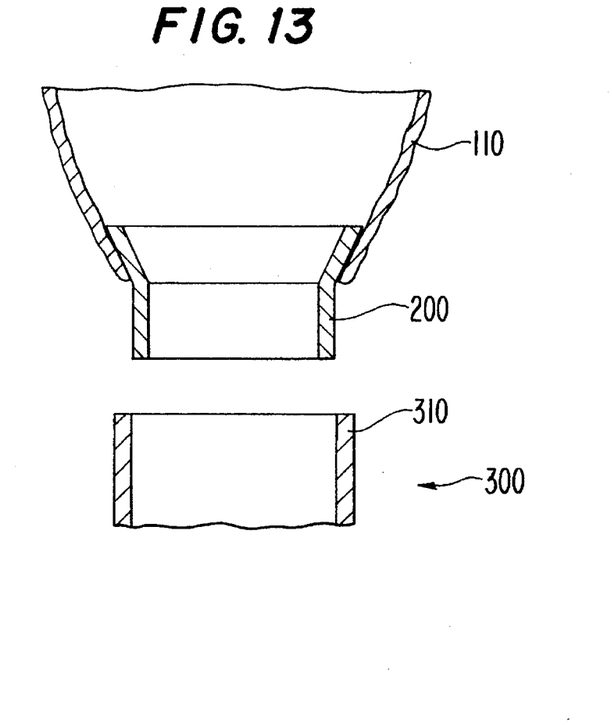
FIG. 13 is an exploded view of a connection between cap and flexible packaging element.

The fixing of the tube shaped packaging element 100 to the cap 300 can be realized with a frame 200 (FIG. 13), which is bonded, welded or pressed to one end 111 of the packaging element and over which the cap 300 can be engaged. This embodiment is advantageous if the cap 300 is only fixed to the packaging element 100 in the hospital and shortly prior to use, because the coupling member 700 is made from an aqueous material and therefore needs to be stored in its own, moistureproof pack. The cap 300 can, however, be fixed to the packaging element 100 already when manufactured. This is particularly advantageous if coupling member 700 is made from plastic, or if it is obviated, such that no moistureproof pack is required.

Figure 14:
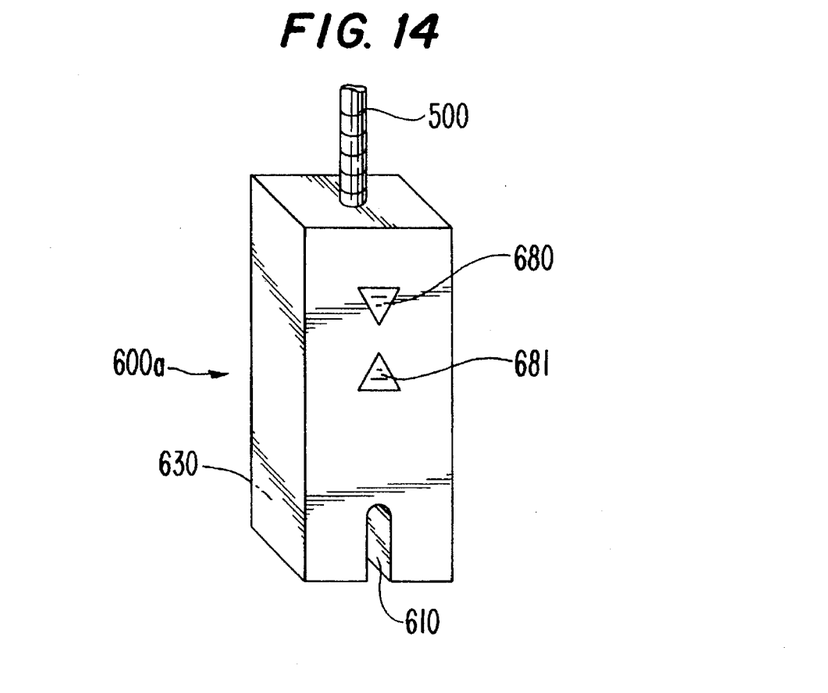
FIG. 14 is a perspective view of an ultrasonic probe.

If the electronics casing is located outside the sterile field, a part of the cable and the probe have to be sterile packed. However, to ensure that the optical directional indication is in the viewing field of the surgeon during puncture, the visual display 680 and 681 must be located on the handle 600a of the ultrasonic probe 600, as shown in FIG. 14.

FIGS. 15 to 18 show a further embodiment of the device according to the invention, with the aid of which the non-sterile Doppler unit can be packed by a non-sterile person alone. In order for the device according to the invention to be used thus, additional parts are required.

Figure 15:
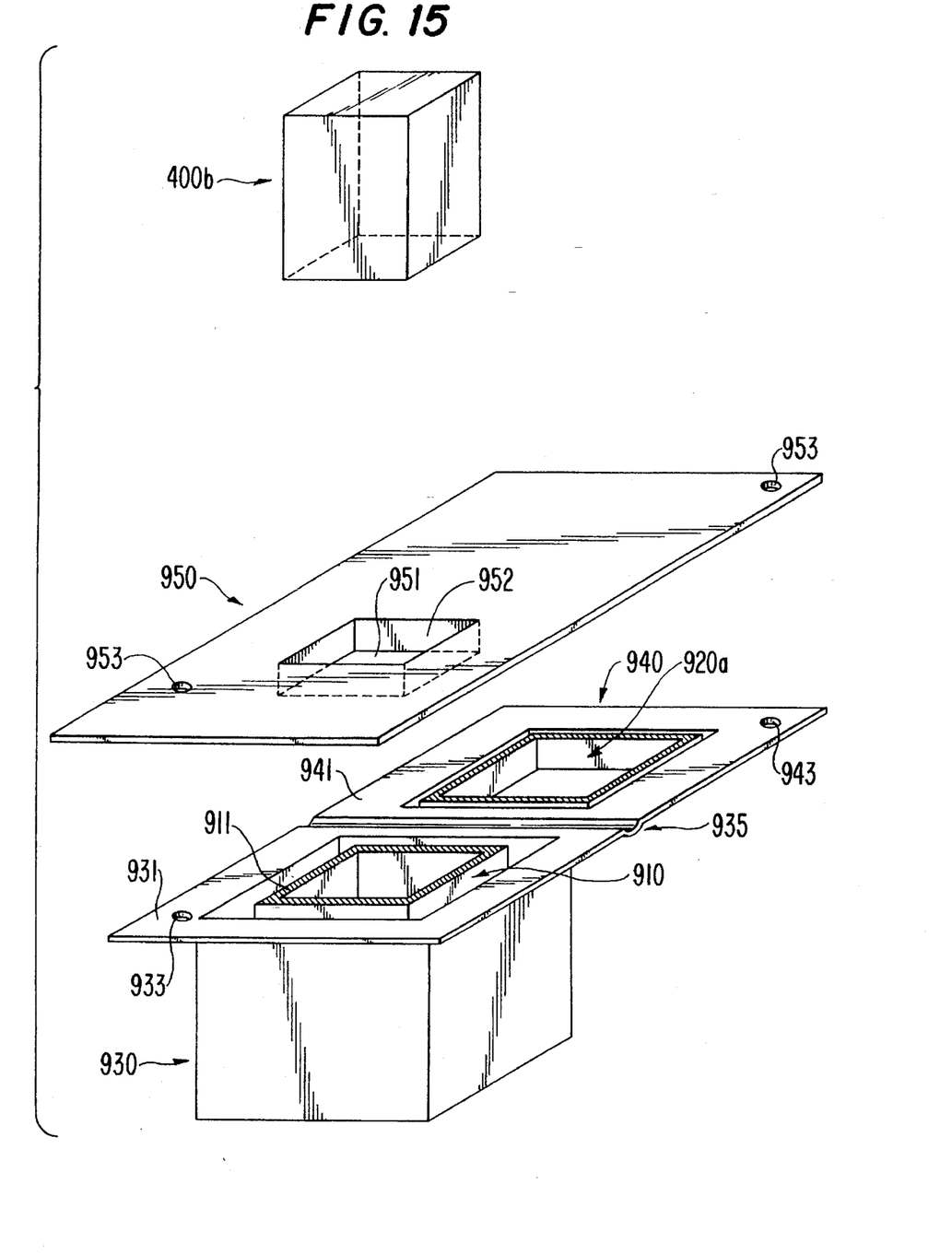
FIG. 15 is an exploded view of a complete embodiment of the device according to the invention.
Figure 16:
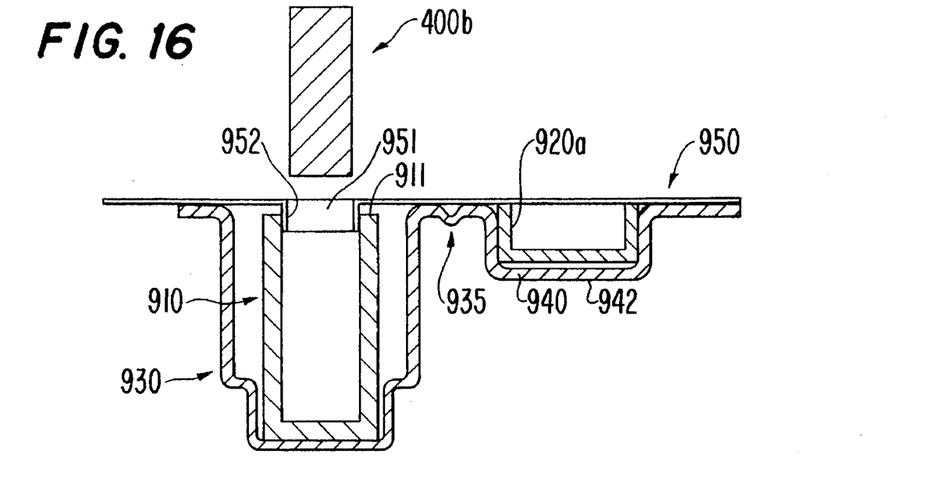
FIGS. 16 to 18 are side elevations, in section, of the device according to FIG. 15 in three different phases of the procedure of packaging the ultrasonic Doppler unit.

FIG. 15 shows the non-sterile Doppler unit 400b (shown here as a prism shaped body), which is to be sterile packed and a total view in perspective of the device according to the invention before its use. In order to allow a better view a protecting cover 950, which protects the device before and during the insertion of the non-sterile unit, is shown in an elevated position. FIG. 16 shows a section of the device with the protecting cover 950 in its actual position.

On the one hand the device has an inner receptacle 910 with a fitting inner cover 920a, which are made in such a way, that together they form the packaging element and the cap (as described above) of the device according to the invention. In other words, the inner receptacle is e.g. made in a way that it forms a cap (not visible) and a partly rigid packaging element fixed to the cap and that the inner cover forms the seal of the packaging element. It is also possible for the inner receptacle to form a sealed packaging element with a connecting frame and for the inner cover to form the cap, which is then fitted onto the connecting frame, when the inner cover is fitted onto the inner receptacle.

On the other hand the device has an outer receptacle 930, an outer cover 940 as well as the protecting cover 950 mentioned above with a recess 951. The inner receptacle 910 is positioned in the outer receptacle 930, the inner cover 920a in the outer cover 940. The outer receptacle 930 and the outer cover 940 are ideally connected with a film hinge 935 and, in the open position shown in FIGS. 15 and 16, are covered by the protecting cover 950 in such a way that the recess 951 is positioned over the opening of the inner receptacle 910.

For the insertion of the ultrasonic Doppler unit a non sterile person holds the outer receptacle in one hand, e.g. the left hand and can hold it with this same hand till the end of the packaging procedure. With the right hand the non-sterile person inserts the non sterile Doppler unit 400b through the recess 951 of the protecting cover 950 into the receptacle 910 (FIG. 16). If the cap forms part of the inner receptacle 910, the Doppler unit is inserted with the probe first, if the cap forms a part of the inner cover, it is inserted the other way around. Contamination of the top rim 911 of the receptacle 910 by the non-sterile Doppler unit 400b or by the non-sterile person is prevented by a lip 952 fixed to the rim of recess 951 of protecting cover 950. A similar protecting function can be achieved by gluing or welding the protecting cover 950 to the top rim 911 of receptacle 910.

The non-sterile Doppler unit 400b is then let go of and thus falls down into the receptacle 910. The non-sterile person then disconnects the protecting cover 950 from the outer receptacle 930 and the outer cover 940. This is possible because the protecting cover 950 is only glued, welded or fixed with pushbuttons 933, 943 and 953 to the inside 931 of the outer receptacle 930 and the inside 941 of the outer cover (FIG. 15).

Figure 17:
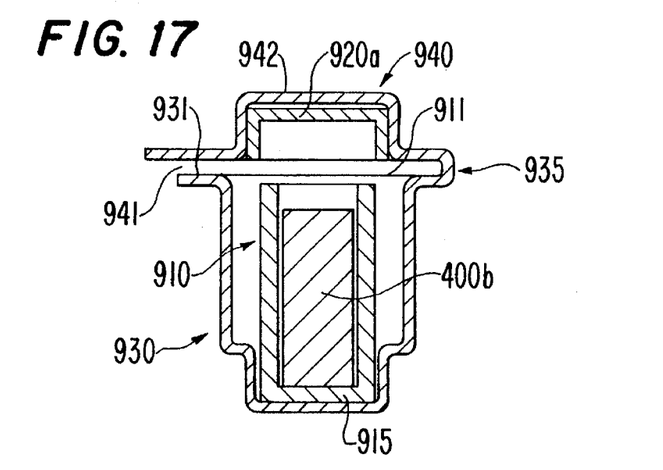

The non-sterile person then closes the outer cover 940 onto the outer receptacle 930, whereby the hinge 935 guides the movement (FIG. 17). During this manipulation the non-sterile person only touches the outside 942 of the outer cover 940. The inside 941 of the outer cover 940, the inside 931 of the outer receptacle 930 and the inner cover 920a remain sterile.

Figure 18:
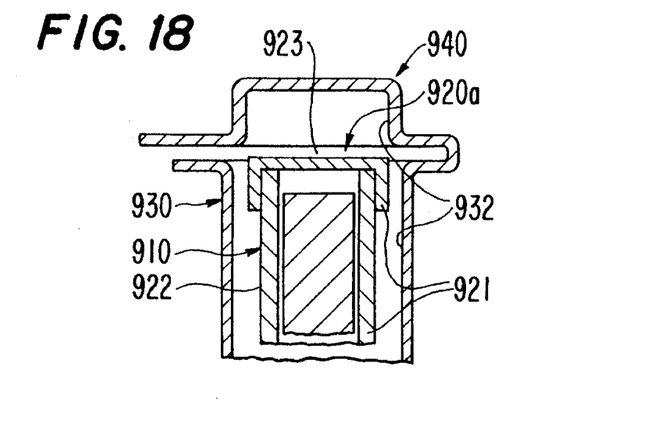

The inner cover 920a is now positioned over the rim 911 and as the outer cover 940 is easily deformable, the non-sterile person can, by applying light pressure to the outer cover 940, deform it in a way that the cover 920a catches on the receptacle 910 (FIG. 18).

The outer receptacle 930 and the outer cover 940 now form a closed cavity, which has a sterile inside 932. This sterile cavity contains the inner receptacle 910 with the caught inner cover 920a, which together form the package 921, of which the outside 922 is sterile. The insertion of the non-sterile Doppler unit is now completed. The whole process can be carried out in less than 20 seconds and is executed in the non-sterile part of the operating theatre.

The non-sterile person then goes into the vicinity of the sterile field, opens the outer cover 940 by means of the right hand and tips over the outer receptacle 930 with the left hand. The package 921, that is sterile on the outside falls downward and is caught by a sterile person. This last step—the sterile handing over of a sterile object into the sterile field—is an everyday hospital routine.

The embodiment of the package according to the invention (FIGS. 15 to 18) can, likewise as the other embodiments, be used for a complete ultrasonic Doppler unit or only for a probe with or without cable or parts of a cable. An embodiment in which only the probe is packed and which features areas that are penetrable by a plug, either on the inner receptacle or on the inner cover, is used together with a sterile cable and a non-sterile electronics unit that is kept outside of the sterile field.

I claim:

1. A device for sterile packing of at least part of an ultrasonic Doppler unit wherein the Doppler unit includes a non-sterile probe having an ultrasonic wave transmission axis, an electronic unit and a cable electrically interconnecting the probe and the electronic unit, the probe having an axial slot with a slot bottom for positioning a hypodermic needle parallel to and substantially coaxial with the axis of ultrasonic waves emitted by the probe, the device comprising the combination of:

a cap having a non-sterile interior volume for receiving at least the distal end of the probe and a sterile exterior surface for facing toward a patient's skin;

a guide tube penetrating said cap from one side to the other side having a sterile interior surface for receiving the hypodermic needle, said guide tube being dimensioned to enter said axial slot and lie at said slot bottom when said distal end of said probe is inserted into said cap; and an exteriorly sterile packaging element for receiving at least said cable of said Doppler unit, said packaging element being attached to said cap and having a closable opening through which said probe and at least part of said cable is insertable.

2. A device according to claim 1 wherein an end of said guide tube extends axially beyond said axial slot, said device further including a coupling member surrounding said end extending beyond said slot.

3. A device according to claim 2 wherein said cap includes a coupling member housing receiving said coupling member.

4. A device according to claim 2 wherein said coupling member comprises a dimensionally stable aqueous gel having a convex surface facing said probe, said coupling member being positioned in said cap so that said convex surface is displaced slightly by a surface of said probe facing toward the skin of a patient when said probe is inserted into said cap.

5. A device according to claim 2 wherein said cap includes small hooks on an inner surface thereof to retain said coupling member.

6. A device according to claim 2 wherein said cap includes pores through a surface thereof to retain said coupling member.

7. A device according to claim 2 wherein said cap includes holes through a wall thereof to retain said coupling member.

8. A device according to claim 2 and including a gauze strip through at least one end of said coupling member to retain said coupling member.

9. A device according to claim 2 and including a membrane at least one end of said coupling member to retain said coupling member.

10. A device according to claim 2 and further including a plate between said coupling member and said probe, said plate being partially transparent to ultrasonic waves emitted by said probe and having at least one curved surface, said plate thereby becoming a lens for focusing ultrasonic waves.

11. A device according to claim 2 wherein said coupling member is a viscous gel, said device including flexible retaining means at opposite ends of said coupling member.

12. A device according to claim 11 wherein said flexible retaining means at an end of said coupling member facing toward a patient's skin is connected to an adjacent end of said guide tube.

13. A device according to claim 2 wherein said coupling member comprises a rigid plastic.

14. A device according to claim 13 wherein an end of said coupling member facing toward a patient's skin is at an angle of between about 30° and 90° with a central axis of said guide tube.

15. A device according to claim 2 and further including a web interconnecting said guide tube to said cap.

16. A device according to claim 1 wherein said packaging element includes a frame shaped and dimensioned to be coupled to said cap.

17. A device according to claim 1 wherein said cap comprises first and second end plates attached respectively to opposite ends of said guide tube, said tube penetrating said end plates, said cap being disposed in said packaging element with said packaging element being attached to said end plates.

18. A device according to claim 1 wherein said cap comprises an inner receptacle having an open end and said packaging element comprises an inner cover dimensioned to close said open end, said device further comprising an outer receptacle, an outer cover, a hinge connecting said outer cover to said outer receptacle, said inner receptacle being received in said outer receptacle and said inner cover being received in said outer cover, a protective cover having an opening therethrough, said protective cover being positionable on said outer receptacle with said opening positioned in alignment with said open end of said inner receptacle.

19. A device according to claim 18 wherein said protective cover is removably attached to said outer receptacle and said outer cover.

20. A device according to claim 19 wherein said outer receptacle and said outer cover have open ends, and wherein said protective cover is removably attached to said open ends of said outer receptacle and said outer cover.

21. A device according to claim 19 wherein said protective cover includes lips around said opening through protective cover, said lips extending into said open end of said inner receptacle.

22. A device according to claim 19 wherein said outer cover is deformable.

\* \* \* \* \*